(12) United States Patent
Courtin

(10) Patent No.: US 8,394,395 B2
(45) Date of Patent: Mar. 12, 2013

(54) USE OF A COSMETIC COMPOSITION FOR THE CARE OF FATTY SKIN

(75) Inventor: Olivier Courtin, Boulogne Billancourt (FR)

(73) Assignee: Laboratories Clarins, Neuilly sur Seine (FR)

( * ) Notice: Subject to any disclaimer, the term of this patent is extended or adjusted under 35 U.S.C. 154(b) by 600 days.

(21) Appl. No.: 12/444,343

(22) PCT Filed: Oct. 5, 2007

(86) PCT No.: PCT/FR2007/001628
§ 371 (c)(1),
(2), (4) Date: May 21, 2010

(87) PCT Pub. No.: WO2008/043900
PCT Pub. Date: Apr. 17, 2008

(65) Prior Publication Data
US 2010/0278948 A1 Nov. 4, 2010

(30) Foreign Application Priority Data
Oct. 6, 2006 (FR) .................................... 06 08785

(51) Int. Cl.
*A61K 31/35* (2006.01)
(52) U.S. Cl. ......... 424/401; 424/642; 424/725; 514/456
(58) Field of Classification Search .................. None
See application file for complete search history.

(56) References Cited

U.S. PATENT DOCUMENTS

| 6,423,747 | B1 | 7/2002 | Lanzendorfer et al. | |
|---|---|---|---|---|
| 2002/0028222 | A1* | 3/2002 | Afriat | 424/401 |
| 2006/0251750 | A1* | 11/2006 | Tabor | 424/757 |

FOREIGN PATENT DOCUMENTS

| DE | 19807774 A1 | 8/1999 |
|---|---|---|
| DE | 10118382 A1 | 10/2002 |
| JP | 01047708 A | 2/1989 |
| JP | 03005423 A | 1/1991 |
| JP | 2000319154 A * | 11/2000 |
| JP | 2001213775 A | 8/2001 |
| WO | 2004089392 A1 | 10/2004 |
| WO | 2005102266 A1 | 11/2005 |

OTHER PUBLICATIONS

T. Mosmann: "Rapid Colorimetric Assay for Cellular Growth and Survival: Application to Proliferation and Cytotoxicity Assays," J. or Immunological Methods, vol. 65, 1983, pp. 55-63.
H. Schaefer: "The Quantitative Differentiation of Sebum Excretion Using Physical Methods," J. Soc. Cosmetic Chemists, vol. 24, 1973, pp. 331-353.

* cited by examiner

*Primary Examiner* — Susan Hoffman
(74) *Attorney, Agent, or Firm* — Rothwell, Figg, Ernst & Manbeck, P.C.

(57) ABSTRACT

The present invention relates to the use of chrysin in a cosmetic composition for the care of fatty skin. The present invention also relates to a cosmetic treatment method for the prophylaxis or therapy of fatty skin that comprises the application onto the skin of a chrysin-containing cosmetic composition.

5 Claims, 2 Drawing Sheets

Figure 1:

|  | Control (OD 570 nm) | $10^{-3}$% CHRYSIN (OD 570 nm) |
|---|---|---|
| Mean | 0.38 | 0.34 |
| Variance | $2.49 \times 10^{-4}$ | $2.65 \times 10^{-4}$ |
| Observations | 6 | 6 |
| Pearson's correlation coefficient | -0.15 | |
| Hypothetical difference in the means | 0 | |
| Degree of freedom | 5 | |
| Statistic t | 4.39 | |
| P(T<=t) one-sided | $3.54 \times 10^{-3}$ | |
| Critical value of t (one-sided) | 2.02 | |
| P(T<=t) two-sided | $7.08 \times 10^{-3}$ | |
| Critical value of t (two-sided) | 2.57 | |

Figure 2:

|  | Control | $5 \times 10^{-3}$% CHRYSIN* |
|---|---|---|
| Mean | 0.38 | 0.29 |
| Variance | $2.49 \times 10^{-4}$ | $3.53 \times 10^{-4}$ |
| Observations | 6 | 6 |
| Pearson's correlation coefficient | 0.64 |  |
| Hypothetical difference in the means | 0 |  |
| Degree of freedom | 5 |  |
| Statistic t | 15.58 |  |
| P(T<=t) one-sided | $9.90282 \times 10^{-6}$ |  |
| Critical value of t (one-sided) | 2.02 |  |
| P(T<=t) two-sided | $1.98056 \times 10^{-5}$ |  |
| Critical value of t (two-sided) | 2.57 |  |

USE OF A COSMETIC COMPOSITION FOR THE CARE OF FATTY SKIN

CROSS REFERENCE TO RELATED APPLICATION(S)

This application is a 35 U.S.C. § 371 National Phase Entry Application from PCT/FR2007/001628, filed Oct. 5, 200, and designating the United States. This application also claims the benefit of French Application No. 0608785, filed Oct. 6, 2006, each of which is incorporated by reference in their entirety.

The present invention relates to the use of a cosmetic composition for preventing or treating problems of greasy skin.

Three main types of skin can be distinguished depending on the hydration of the horny layer and the sebum production thereof: dry skin, greasy skin and mixed skin.

Knowledge of the various types of skin makes it possible to adapt an appropriate cosmetic treatment for each case.

The skin is made up, inter alia, of sebaceous glands located in the dermis and almost always associated with a hair. All the parts of the body have them, with the exception of the sole of the foot and the palm of the hand. Certain areas, such as the face, the scalp or the chest, have a larger number of them (approximately five million). These sebaceous glands secrete sebum which flows along the hair canal to the surface of the skin, where, in contact with sweat, it forms the hydrolipidic film which hydrates the horny layer and protects it.

The sebaceous gland is an acinar gland in the form of a cluster. It is made up of numerous cell layers in which two types of cells are found: undifferentiated cells (germinative layer), located toward the periphery of the gland, which actively divide. These cells migrate in approximately 2 weeks to the centre so as to give differentiated cells; central differentiated cells (sebocytes) which contain the enzymatic equipment necessary for lipid synthesis. These cells no longer divide. In one week they become converted to larger mature cells, filled with sebum; the lipids therein are synthesized and stored so as to finally constitute large vacuoles.

In humans, each follicle develops according to its own cycle, i.e. one gland may atrophy while another hypertrophies. The renewal time for sebocytes is approximately 3 weeks.

The gland volume depends on the proliferative activity of the germinative compartment, on the time required for differentiation of the sebocyte and on the quality of the sebum synthesized by each sebocyte.

Sebum is produced in a more or less large amount depending on the size and the number of the sebaceous glands. Too abundant a secretion leads to modification of the skin: it becomes greasy with a shiny appearance, and has a thick texture and dilated pores, sometimes with blackheads.

In addition to the relatively unaesthetic nature of shiny skin, it should be noted that greasy skin also has a tendency to be easily irritable and holds makeup very poorly. There exists therefore a need for a cosmetic composition capable of limiting sebum production in order to maintain the "normal skin" characteristics of the skin surface. Several cosmetic compositions capable of offering a solution to the problems of greasy skin have been proposed in the prior art. These compositions often contain powders which make it possible to absorb the sebum and therefore to make the skin matt by a mechanical effect, or keratolytic agents for promoting the expulsion of the horny plugs. Astringent active agents for combating sebaceous follicle dilation, or exfoliant active agents for reducing skin thickness, also exist.

However, the effectiveness of these compositions is relative, since most of them do not limit sebum production but merely absorb the sebum via a pumping effect. In addition, most of these compositions only have a curative effect and do not make it possible to prevent the phenomenon in the longer term. Finally, active sulfur, which is effective with respect to the regulation of sebum production, cannot generally be used in a cosmetic composition because of its unpleasant smell.

There remains therefore the need for a cosmetic composition which makes it possible to prevent and treat the problems of greasy skin and which does not act on the symptoms of greasy skin, but on the causes thereof.

The applicant has demonstrated the activity of chrysin on sebum production. Specifically, chrysin is capable of regulating the proliferation of human sebocytes, and of delaying their differentiation into mature sebum-producing cells. Since there are fewer sebum-producing cells, there is less sebum production and, consequently, the amount of sebum poured out by the sebaceous glands at the skin surface is reduced. The skin then no longer has the unattractive characteristics of greasy skin. Chrysin has both a curative action and a preventive action since it makes it possible to modulate sebum production in the long term.

The present invention therefore relates to the use of chrysin in a cosmetic composition or for the preparation of a dermatological composition for use in the care of greasy skin.

The present invention also relates to the use of chrysin in a cosmetic composition or for the preparation of a dermatological composition which regulates greasy skin, and in particular the use of chrysin in a cosmetic composition or for the preparation of a dermatological composition as an agent for regulating greasy skin.

The present invention also relates to the use of chrysin in a cosmetic composition or for the preparation of a dermatological composition which regulates sebum production, and in particular the use of chrysin in a cosmetic composition or for the preparation of a dermatological composition as an agent for regulating sebum production.

The present invention also relates to the use of chrysin in a cosmetic composition or for the preparation of a dermatological composition which regulates sebocyte proliferation, and in particular the use of chrysin in a cosmetic composition or for the preparation of a dermatological composition as an agent for regulating sebocyte proliferation.

The present invention also relates to the use of chrysin in a cosmetic composition or for the preparation of a dermatological composition which is a purifying and/or mattifying composition, and in particular the use of chrysin in a cosmetic composition or for the preparation of a dermatological composition as a purifying and/or mattifying agent. Finally, the present invention relates to the use of chrysin in a cosmetic composition or for the preparation of a dermatological composition which is an anti-shine protecting composition, and in particular the use of chrysin in a cosmetic composition or for the preparation of a dermatological composition as an anti-shine protecting agent.

Chrysin is already used in cosmetics as an antiviral agent combined with a sunscreen in patent application EP 0980684. The use of chrysin as a free-radical scavenger is also described in patent FR 2687572. Surprisingly, the applicant has demonstrated the regulatory action of chrysin on the differentiation and proliferation of human sebocytes.

Chrysin, also known as 5,7-dihydroxyflavone, is a molecule with a molecular weight of 254.23 g/mol.

Advantageously, the chrysin that can be used in the context of the present invention is obtained by chemical synthesis and is commonly available. It is an odour less powder which is light yellow in color and has a maximum water content of 2% and a molecular weight of 254.23 g/mol. Since chrysin is present in many plants, a chrysin of natural origin can also be used.

The chrysin that can be used according to the invention can, for example, be obtained from the company DKSH France, where it is marketed under the name "chrysin".

According to the invention, chrysin can be used with one or more other active agents having properties for combating greasy skin. In particular, chrysin can be combined, in a cosmetic or dermatological composition, with an extract of white deadnettle, also known as *Lamium album*. In fact, white deadnettle has a sulfur content of greater than 200 ppm. Since sulfur is capable of regulating sebum production, the use of an extract of white deadnettle, in particular a glycolic extract, makes it possible to have sulfur in the cosmetic composition of the invention without having the drawback in terms of the unpleasant odor. The extract may also be a sulfur-rich fraction of an extract of white deadnettle, provided, of course, that this fraction does not have the unpleasant odor.

Similarly, the chrysin may be combined, in a cosmetic or dermatological composition, with an extract of *Hamamelis virginiana* known for its astrigent properties, and/or with pyridoxine hydrochloride or vitamin B6, which reduces the flow of sebum and normalizes the pH of greasy skin, and/or with zinc derivatives which have both an astringent activity and a recognized fungicidal and bactericidal efficacy. The term "zinc derivatives" is intended to mean zinc salts, and in particular zinc sulfate and zinc gluconate.

The composition according to the invention contains about 0.001% to 1% by weight, and preferably 0.001% to 0.01% by weight of chrysin.

The cosmetic composition of the present invention for topical application may in particular constitute a cosmetic or dermatological protecting, cleansing, treating or care composition for the face, for the neck or for the body, for instance day creams, night creams, face lotions, masks, foaming cleansing gels, body milks, a hair composition (for example, a scalp lotion), or a makeup composition (for example, foundation, tinted cream).

The cosmetic composition according to the present invention may contain one or more other components known to those skilled in the art, such as formulating agents or additives for use, known and conventional in cosmetic compositions. By way of nonlimiting example, such formulating agents and additives may be hydrophilic or lipophilic gelling agents, softeners, dyes, solubilizing agents, texturing agents, fragrances, fillers, film-forming active agents, preservatives, surfactants, emulsifiers, oils, glycols, vitamins, sunscreens, etc. By virtue of their knowledge in terms of cosmetics, those skilled in the art will know which formulating agents to add to the cosmetic composition according to the invention, and in what amounts, depending on the desired properties.

Furthermore, the cosmetic composition according to the present invention may be in any form known to those skilled in the art in the cosmetics field, without any particular galenic restriction other than that for application to the skin. Thus, the cosmetic composition according to the invention may be in the form of an aqueous or alcoholic solution or suspension or an oily suspension or a solution or dispersion of lotion or serum type, an emulsion which has a liquid or semi-liquid consistency, of the milk type, obtained by dispersion of a fatty phase in an aqueous phase (oil-in-water emulsion: O/W) or vice versa (water-in-oil: W/O), an emulsion of the O/W or W/O cream type or a gel, a lotion or a mask. The cosmetic formulations according to the invention can also be envisioned in the form of a foam or alternatively in the form of aerosol compositions, also comprising a pressurized propellant.

The present invention also relates to a cosmetic treatment method for preventing or treating problems of greasy skin, comprising the application to the skin of a cosmetic composition containing chrysin.

The present invention also relates to the use of chrysin for the preparation of a dermatological composition for use in preventing or treating problems of greasy skin.

The examples hereinafter concern, on the one hand, the evaluation of the effect of chrysin on the proliferation of human sebocytes in culture and, on the other hand, compositions which are subjects of the present invention.

The examples make reference to the following figures in which:

FIG. 1 represents the test for equality of means: paired observations for a chrysin concentration of $10^{-3}$%.

FIG. 2 represents the test for equality of means: paired observations for a chrysin concentration of $5 \times 10^{-3}$%.

I. EVALUATION OF THE INHIBITION BY CHRYSIN OF THE PROLIFERATION OF HUMAN SEBOCYTES IN CULTURE

A. Materials and Methods

1. Sebocyte Culture

A line of human sebocytes (Hs 917.T, ATCC line No. CRL-7669) was cultured in Dulbecco's modified Eagle's medium with 4.5 g/l of D-glucose and 10% of fetal calf serum. These adherent cells have a polygonal morphology and large nuclei.

They proliferate, increasing in size, and progressively differentiate.

2. Evaluation of Sebocyte Proliferation

Proliferation was evaluated by means of a validated colorimetric test, the M.T.T. test (dimethyl thiazolyl diphenyl tetrazolium) (according to Mosmann, J. Immunol. Meth. 1983 65: 55-63). This compound is metabolized by the mitochondria, to give blue formazan crystals, the amount of which depends directly on the activity of the mitochondrial succinate dehydrogenase enzyme and on the number of living cells.

As a result of this, the proliferation is measured by colorimetery (570 nm).

3. Bringing the Sebocytes into Contact with Chrysin

Firstly, we verified the viability (MTT exclusion test) of the sebocytes in the presence of chrysin at various concentrations, in comparison with their conventional culture medium. The results show that chrysin applied, at concentrations of $10^{-3}$% and $5 \times 10^{-3}$%, to sebocytes did not induce any cytotoxicity on these cells.

The proliferation was therefore evaluated according to the following conditions:
- sebocytes in reference medium;
- sebocytes cultured in the presence of the reference medium supplemented with chrysin at the 2 concentrations of $10^{-3}$% and $5 \times 10^{-3}$%.

For each condition performed in sextuplet, the proliferation was analyzed after 72 hours of culture.

B. Results

An inhibitory effect of chrysin on the proliferation of human sebocytes in culture is observed: difference of −10.5% for a chrysin concentration of $10^{-3}$% and of −18.4% for a concentration of $5 \times 10^{-3}$%.

By inhibiting sebocyte proliferation, chrysin reduces sebum production. Since there is less sebum poured out at the skin surface, the skin goes back to the characteristics of "normal skin".

II. EXAMPLES

In the following examples, the chrysin is solubilized beforehand in a solution of 2% WATER and 0.004% NaOH (hereinafter referred to as SOL), before being added to the cosmetic composition.

A. Cream for Greasy Skin

|  | % |
|---|---|
| XANTHAN GUM | 0.10 |
| GLYCEROL | 5.00 |
| CETEARYL GLUCOSIDE | 3.00 |
| GLYCERYL MONOSTEARATE AE | 2.00 |
| $C_8C_{10}$ TRIGLYCERIDE | 10.00 |
| SILICONE OIL | 3.00 |
| ZINC GLUCONATE | 0.02 |
| PYRIDOXINE HYDROCHLORIDE | 0.10 |
| CHRYSIN solubilized in SOL | 0.0016 |
| PRESERVATIVES | 1.00 |
| FRAGRANCE | 0.30 |
| DEMINERALIZED WATER | Q.S. 100 |

B. Gel for Greasy Skin

|  | % |
|---|---|
| GLYCEROL | 3.00 |
| XANTHAN GUM | 0.20 |
| ETHANOL | 5.00 |
| ZINC GLUCONATE | 0.02 |
| PYRIDOXINE HYDROCHLORIDE | 0.10 |
| CHRYSIN solubilized in SOL | 0.0016 |
| PRESERVATIVES | 0.50 |
| SOLUBILIZING AGENT | 0.50 |
| FRAGRANCE | 0.20 |
| DEMINERALIZED WATER | Q.S. 100 |

C. Lotion for Greasy Skin

|  | % |
|---|---|
| GLYCOL | 2.00 |
| SODIUM CHLORIDE | 1.00 |
| ETHANOL | 5.00 |
| ZINC GLUCONATE | 0.02 |
| PYRIDOXINE HYDROCHLORIDE | 0.10 |
| CHRYSIN solubilized in SOL | 0.0016 |
| PRESERVATIVES | 0.50 |
| SOLUBILIZING AGENT | 0.30 |
| FRAGRANCE | 0.10 |
| DEMINERALIZED WATER | Q.S. 100 |

The invention claimed is:

1. A cosmetic or dermatological treatment method for preventing or treating greasy skin in a subject in need thereof, comprising reducing skin shine, regulating skin sebum production and regulating skin sebocyte proliferation by applying to the subject's skin a cosmetic or dermatological composition containing chrysin, wherein said composition is applied in an amount sufficient to act as a mattifying agent, reduce skin shine, regulate skin sebum production and regulate skin sebocyte proliferation.

2. The method of claim 1, wherein said composition comprises a solution, suspension, dispersion, lotion, serum, emulsion, liquid, semi-liquid having consistency of milk, cream, gel, lotion, mask, foam or aerosol.

3. The method of claim 1, wherein said composition contains about 0.001% to 1% by weight of chrysin.

4. The method of claim 1, wherein said composition contains about 0.001% to 0.01% by weight of chrysin.

5. The method of claim 1, wherein said composition further contains at least one active agent chosen from an extract of Lamium album, an extract of Hamamelis virginiana, pyridoxine hydrochloride and zinc derivatives.

* * * * *